United States Patent
Vernon

(10) Patent No.: US 8,075,538 B2
(45) Date of Patent: Dec. 13, 2011

(54) URINE RECEPTACLE AND APPARATUS FOR AUTOMATED DISPOSAL OF URINE

(76) Inventor: Robert D Vernon, Denver, CO (US)

( * ) Notice: Subject to any disclaimer, the term of this patent is extended or adjusted under 35 U.S.C. 154(b) by 467 days.

(21) Appl. No.: 11/119,734

(22) Filed: May 3, 2005

(65) Prior Publication Data

US 2006/0253091 A1 Nov. 9, 2006

(51) Int. Cl.
*A61M 1/00* (2006.01)
(52) U.S. Cl. .................. 604/322; 604/317
(58) Field of Classification Search .......... 604/317, 604/322–326, 327, 349–351, 353, 385.19; 280/250.1
See application file for complete search history.

(56) References Cited

U.S. PATENT DOCUMENTS

| | | | | |
|---|---|---|---|---|
| 15,192 A * | 6/1856 | Peale | .................. | 137/844 |
| 2,496,175 A * | 1/1950 | Murle | .................. | 604/335 |
| 2,759,477 A * | 8/1956 | Mains | .................. | 604/343 |
| 3,608,268 A * | 9/1971 | Lauritzen | .................. | 53/452 |
| 4,204,527 A | 5/1980 | Wu et al. | | |
| 4,386,930 A | 6/1983 | Cianci | | |
| 4,421,509 A * | 12/1983 | Schneider et al. | .................. | 604/317 |
| 4,496,354 A | 1/1985 | Steer et al. | | |
| 4,511,358 A | 4/1985 | Johnson, Jr. et al. | | |
| 4,533,354 A | 8/1985 | Jensen | | |
| 4,592,750 A * | 6/1986 | Kay | .................. | 604/337 |
| 4,604,095 A * | 8/1986 | Samuelsen | .................. | 604/323 |
| 4,790,833 A * | 12/1988 | Schmidt | .................. | 604/317 |
| 4,828,553 A * | 5/1989 | Nielsen | .................. | 604/339 |
| 4,828,554 A | 5/1989 | Griffin | | |
| 4,838,883 A * | 6/1989 | Matsuura | .................. | 604/349 |
| 4,957,487 A * | 9/1990 | Gerow | .................. | 604/133 |
| 5,107,859 A * | 4/1992 | Alcorn et al. | .................. | 128/853 |
| 5,226,564 A | 7/1993 | Steer et al. | | |
| 5,234,420 A * | 8/1993 | Horton et al. | .................. | 604/345 |
| 5,267,987 A | 12/1993 | Fabricant | | |
| 5,267,989 A | 12/1993 | Moyet-Ortiz | | |
| 5,318,549 A | 6/1994 | Yang | | |
| 5,337,924 A * | 8/1994 | Dickie | .................. | 222/212 |
| 5,374,257 A | 12/1994 | Drainville et al. | | |
| 5,375,265 A | 12/1994 | Selzer | | |
| 5,439,456 A | 8/1995 | Fabricant | | |
| 5,643,236 A | 7/1997 | Hadley | | |
| 5,934,345 A * | 8/1999 | Moynihan et al. | .................. | 141/313 |
| 6,012,181 A * | 1/2000 | Johnson et al. | .................. | 4/480 |
| 6,152,903 A * | 11/2000 | Falconer | .................. | 604/351 |
| 6,526,603 B1 | 3/2003 | Murphy | | |
| 6,530,909 B1 | 3/2003 | Nozaki et al. | | |
| 7,066,918 B2 * | 6/2006 | Charles | .................. | 604/327 |
| 2006/0079854 A1 * | 4/2006 | Kay et al. | .................. | 604/328 |

FOREIGN PATENT DOCUMENTS

WO WO8705493 9/1987

* cited by examiner

*Primary Examiner* — Melanie Hand
(74) *Attorney, Agent, or Firm* — The Harris Firm

(57) ABSTRACT

A disposable re-useable urine receptacle that, when used, provides comfortable, discrete, and safe urine collection and containment until the collected urine can be properly disposed of, either by the wearer or someone else. It achieves these goals by conforming to the wearer's body, expanding to a predetermined self-supported shape, and disallowing side wall-to-wall adherence between fillings. An apparatus for automated disposal of urine is also disclosed.

34 Claims, 8 Drawing Sheets

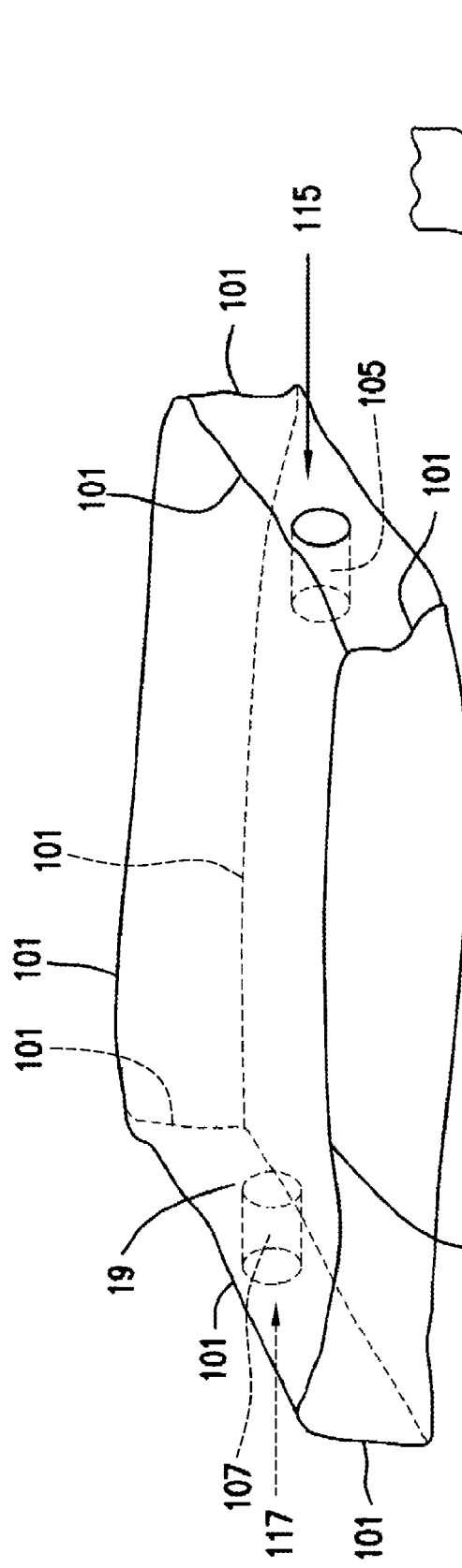
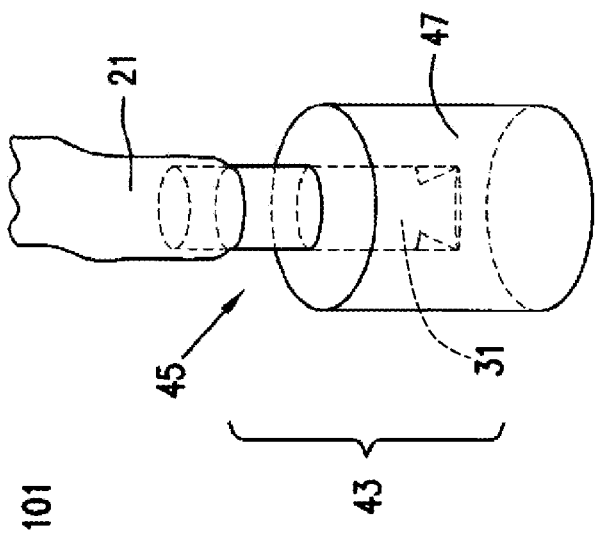
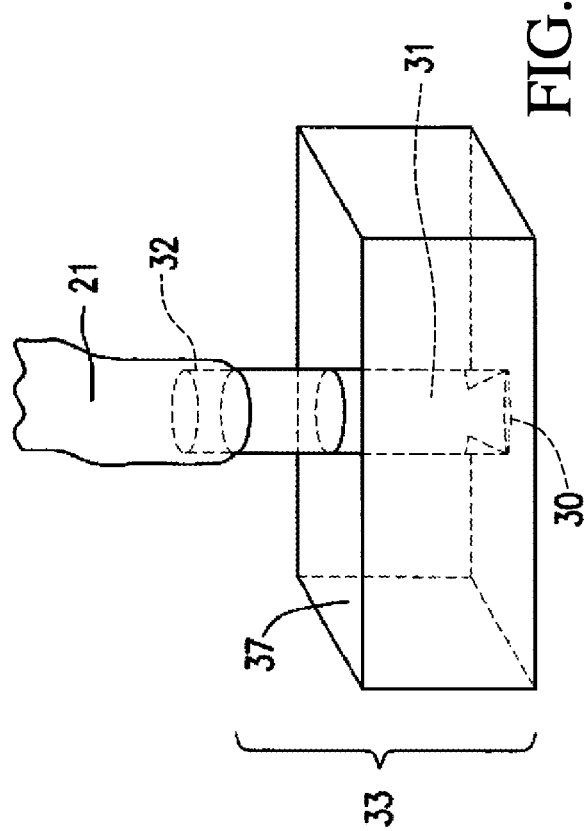
FIG. 1a
FIG. 1b
FIG. 1c

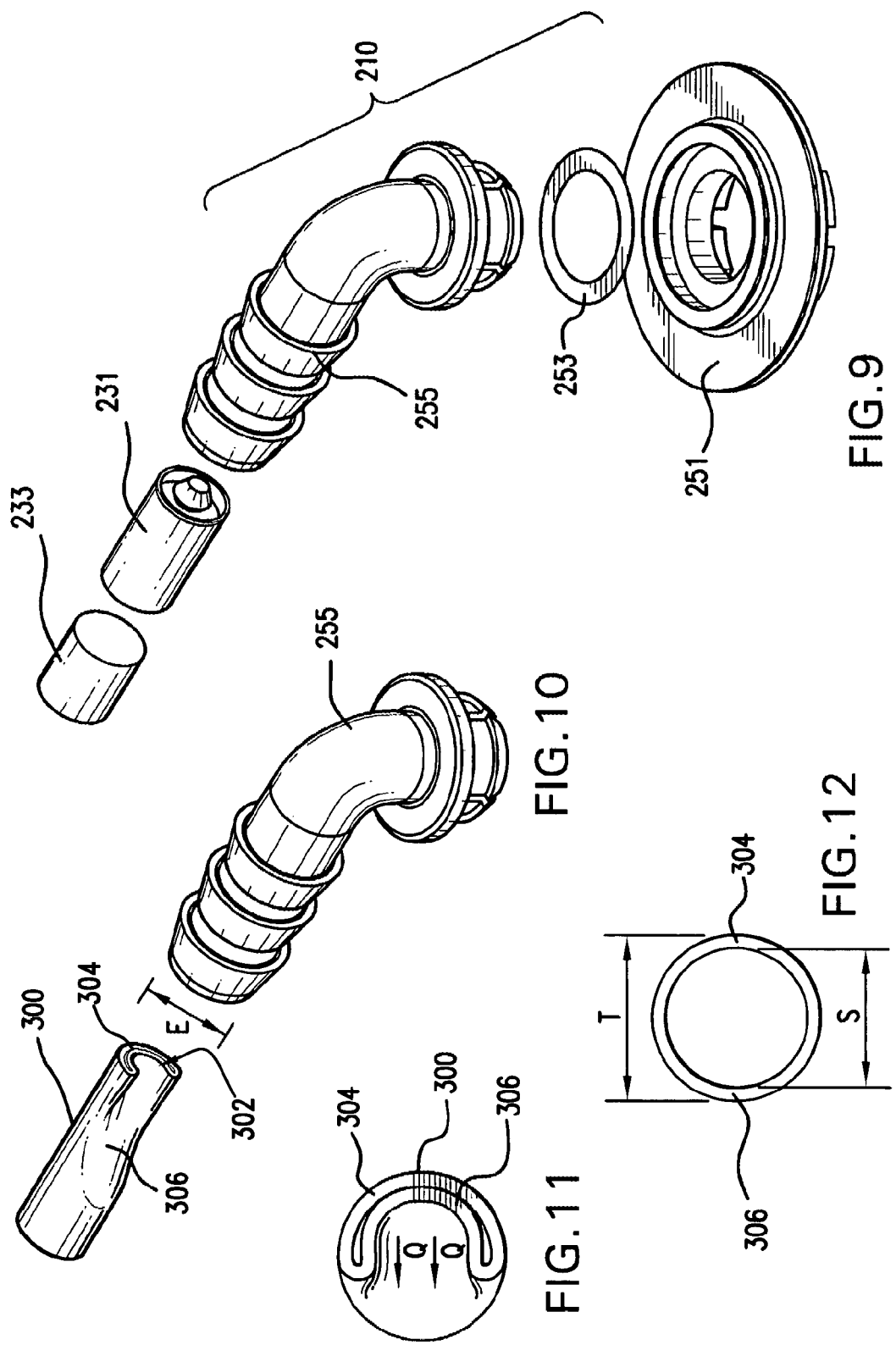

URINE RECEPTACLE AND APPARATUS FOR AUTOMATED DISPOSAL OF URINE

FIELD OF THE INVENTION

The present invention relates to a urine receptacle and apparatus for the automated disposal of bodily fluid. More particularly, the present invention relates to a reusable, disposable urine receptacle and apparatus for automated disposal of urine, which together provide the wearer increased mobility, comfort, discretion, and ease of use.

BACKGROUND OF THE INVENTION

Existing plastic urinary bags, worn on the thigh or calf, are typically of a design that has remained largely unchanged since such bags were first introduced. An exemplary bag is constructed of two pieces of identically sized and shaped plastic film that is sealed in such a manner as to create a rectangular, flat vessel with an inlet valve at the top and an outlet valve at the bottom. The valves are sealed in place between the two layers of plastic film. To attach the bag to the user's thigh or calf, slits are made at the four corners of the bag to permit the insertion of an adjustable strap (both top and bottom). This strap is usually made of latex rubber or some similar material to which a plastic "button" has been attached. Holes on the strap permit the user to adjust the tension of the strap by stretching the appropriate hole over the button, thus establishing a fixed degree of tension corresponding to the circumference of the leg to which the bag is attached.

Because of the design of such bag, when it is filled with urine it expands to form a rectangular balloon with the surface area of the bag in contact with the leg decreasing steadily in proportion to the volume of liquid contained within the bag. Thus, as the bag fills, it expands in such a manner as to press against the clothing raising the clothing well above the surface of the skin. This tends to make the bag obvious to others, which can be embarrassing to the user. Further, as the bag fills, the force holding the bag in place shifts almost exclusively to the straps, which accentuates the pressure already exerted by the buttons against the user's skin, to cause sores.

In addition, because such bag is constructed of identically sized and shaped sheets of plastic, reuse of the bag after emptying becomes problematic when the two wet surfaces come in contact with one another. The surface tension of the liquid tends to cause the two sides of the bag to stick together, even despite some surface texturing found in some bags. The force required to separate the two sides, which is required to allow the bag to be filled, is sometimes greater than the force exerted by the flow of urine into the bag. Thus, the tendency for the sides to stick together can cause the flow of urine into the bag to be stopped completely with potentially serious health consequences. For those with external catheters, this result can alternatively lead to failure of the catheter itself, which will result in the urine flowing freely onto the leg, clothing, and chair.

Current inlet valves used to prevent backflow add to this problem as well. When the sides of the bag stick together at the top of the bag, they impinge upon the valve because the valve extends into the bag itself. The force required to open the valve therefore includes the force required to open the inlet valve itself and to separate the bag sides from the valve opening. For example, a flat flutter valve that extends into the bag can be affected by pressure exerted against it by the closed sides of the bag. These sides often impinge upon the valve, which interferes with, and sometimes blocks, the flow of urine into the bag. Impingement on these valves also occurs to hinder urine flow when any object is placed on top of the bag, including the user's arms or hands when the bag is worn on the user's thigh.

Current inlet tubes also hinder the flow of urine by causing misalignment between the bag and the catheter that carries the urine. The placement of inlet tubes on existing bags is along the central axis of the bag such that placement of the bag on the user's thigh causes the inlet tubes to point away from the point at which the catheter is inserted or attached to the user. The resulting misalignment often causes the catheter to become constricted as a result of a very small radius bend that forms where the catheter enters the inlet tube. This constriction, like the aforementioned side wall sticking and valve impingement, can interfere with and sometimes block the flow of urine into the bag, which leads to serious health consequences.

SUMMARY OF THE INVENTION

One aspect of the present invention is directed to a urine receptacle that comprises a first side that operatively conforms to a wearer's body; a collapsible second side that expands as the receptacle is filled; wherein the receptacle is self-supporting and, as the receptacle is filled, the distance between the first side and the second side does not substantially vary along a horizontal distance.

In another aspect, once the receptacle is operatively filled, the distance between the first side and the second side does not substantially vary along a vertical distance.

In yet another aspect, the second side comprises a preformed tray.

In still another aspect, the tray has pleats or seams.

In another aspect, the tray has concentric ridges.

In yet another aspect, the first side has a perimeter that is operatively attached to a sleeve on the wearer's leg by hook and loop fasteners.

In still another aspect, the second side and the sleeve comprise hook compatible surfaces that are mated by a piece having double-sided hook material.

In yet another aspect, the receptacle has a spacer that keeps the first and second sides from adhering to each other.

In still another aspect, the receptacle has an inlet valve encased by a shroud that prevents interference with the valve.

In yet another aspect, the receptacle is reusable and is operatively connected to a device for automatically disposing urine.

In still another aspect, the receptacle is operatively connected to the device by at least one non-drip fitting.

In yet another aspect, the receptacle has an outlet that is operatively connected to a pump that works to empty the receptacle.

In still another aspect, the pump has a safety switch and is mounted onto a wheelchair.

In yet another aspect, the receptacle is operatively connected to a waste-directing wand.

Another aspect of the invention is directed to an apparatus for automatic waste disposal, operatively comprising a receptacle having a first side that operatively conforms to a wearer; and a collapsible second side that expands as the receptacle is filled; wherein the receptacle is self-supporting and, as the receptacle is filled, the distance between the first side and the second side does not substantially vary along a horizontal distance.

In another aspect, once the receptacle is operatively filled, the distance between the first side and the second side does not substantially vary along a vertical distance.

In still another aspect, the second side comprises a pre-formed tray.

In yet another aspect, the tray is pleated.

In still another aspect, the tray comprises a polyolefin, polyester, or polyvinylchloride film.

In yet another aspect, the first side has a perimeter that is operatively attached to a sleeve on the wearer's leg by hook and loop fasteners.

In still another aspect, the second side and the sleeve comprise hook compatible surfaces that are mated by a piece having double-sided hook material.

In yet another aspect, the receptacle has a spacer that keeps the first and second sides from adhering to each other.

In still another aspect, the receptacle has a one-way inlet valve encased by a shroud fitment to which an inlet tube or catheter is attached.

In yet another aspect, the receptacle is reusable and is operatively connected to a device for automatically disposing urine.

In still another aspect, the receptacle is operatively connected to the device by at least one non-drip fitting.

In yet another aspect, the receptacle has an outlet that is operatively connected to a pump that works to empty the receptacle.

In still another aspect, the pump has a safety switch and is mounted onto a wheelchair.

In yet another aspect, the receptacle is operatively connected to a waste-directing wand.

Another aspect of the invention is directed to a urine receptacle, comprising a first side that operatively conforms to a wearer; and a collapsible second side that expands as the receptacle is filled; wherein the receptacle is self-supporting and the second side comprises a pre-formed, expandable tray.

In another aspect, the first side does not expand.

In still another aspect, the second side comprises a pre-formed tray that expands and contracts as the receptacle is filled and emptied of liquid.

In yet another aspect, the urine receptacle further comprises an inlet fitting that aligns a receptacle inlet with a catheter attachment or insertion point.

In still another aspect, the fitting is an elbow fitting that swivels to align the inlet with the catheter attachment or insertion point.

In yet another aspect, the urine receptacle further comprises a valve and a shroud, wherein the valve operatively expands to conform, or nearly conform, to the internal dimensions of the shroud.

BRIEF DESCRIPTION OF THE DRAWINGS

In the accompanying drawings, which form a part of the specification and are to be read in conjunction therewith, and in which like reference numerals are used to indicate like parts in the various views:

FIG. 1a is the shrouded inlet assembly of FIG. 1;

FIG. 1b is an alternate embodiment of a shrouded inlet assembly, according to the present invention;

FIG. 1c is an alternate embodiment of a urine receptacle outer tray, according to the present invention;

FIG. 9 is a perspective assembly view of the inlet nozzle assembly of FIG. 4, and a one-way valve and filter according to the present invention;

FIG. 10 is a perspective assembly view of the fitting of FIG. 4 and alternate embodiment of a one-way valve, according to the present invention;

FIG. 11 is a plan end view of the one-way valve from FIG. 10 when closed; and

FIG. 12 is a plan end view of the one-way valve from FIG. 10 when open.

DETAILED DESCRIPTION OF THE INVENTION

As illustrated in the accompanying drawings and discussed in detail below, one aspect of the present invention is directed to a urine receptacle that, when used and worn, provides comfortable, discrete, and safe urine containment until it can be properly disposed, either by the wearer or someone else. It achieves these goals by conforming to the wearer's body, expanding to a predetermined self-supported shape, and disallowing side wall-to-wall adherence between fillings.

One embodiment is directed to a urine receptacle that conforms to the wearer's body and does not lift apart from the wearer as it is filled.

Figure 1:
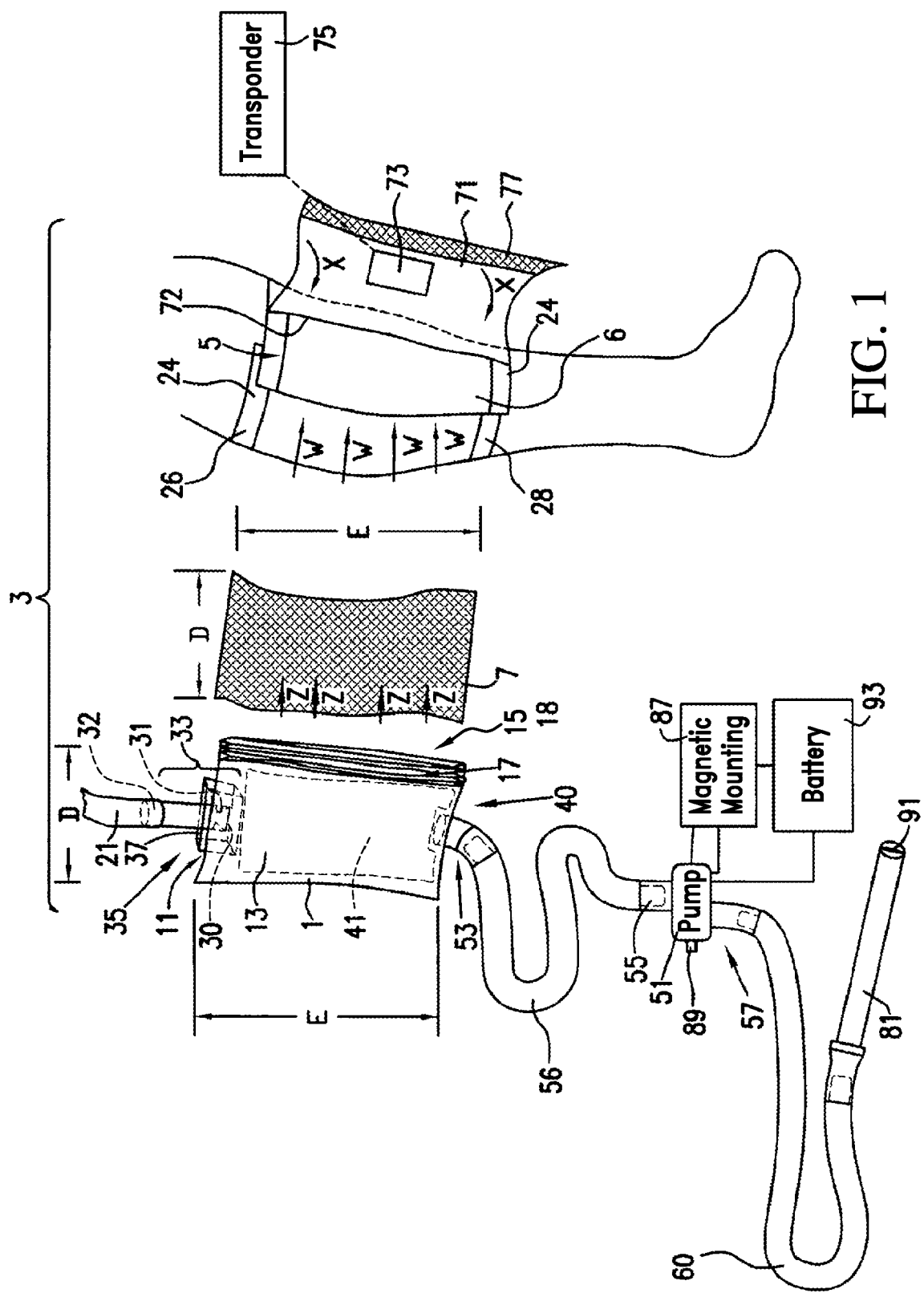
FIG. 1 is a perspective assembly view of an attachment device for a urine receptacle, a urine receptacle, and an apparatus for disposing urine, according to the present invention.

At least one urine receptacle of this embodiment conforms to the shape of the user's thigh or calf by ensuring that the entire surface of the bag side normally held against the skin is firmly attached to the leg. Referring to FIG. 1, urine bag 1 attachment device 3 comprises sleeve 5, double-sided hook material piece 7, and urine bag 1. Sleeve 5 is securely wrapped and fastened via hook and loop materials around the user's calf (or other body part, e.g., thigh). Strips 24 of hook material are sewn onto the top and bottom edges 26 and 28 of hook-friendly material 6 to create sleeve 5. The user thereby wraps sleeve 5 around, and secures sleeve 5 to, a leg. This attachment device is easy to use for the user, especially if the user is sick or weak. In an alternate embodiment, a pre-sewn neoprene (or a breathable elastic) fabric sleeve with hook-friendly or loop-friendly surface (not shown) is pulled up and securely positioned around the user's calf (or other body part, e.g., thigh).

The outer surfaces of sleeve 5 and inner side 11 of bag 1 are "hook friendly", e.g., comprise, are coated with, bonded to, laminated to, or otherwise attached to, a loop fabric such as a micro-fiber cloth or nylon tricot. Double-sided hook material piece 7 has the same shape as inner side 11 of bag 1 (as shown by respective distance arrows D and E). It connects sleeve 5 and bag 1 so that the entire outer perimeter and surface of inner side 11 is securely fastened, and thus conforms, to sleeve 5. More specifically, the user mates one side of hook material piece 7 to the hook friendly surface of inner side 11 in accordance with direction arrows Z, thus removably attaching one to the other. When bag 1 with hook material piece 7 is then positioned on top of the sleeve in accordance with direction arrows W, bag 1 and sleeve 5 are removably attached to one another, thus firmly holding bag 1 in place while causing it to conform to the shape of the wearer's leg.

In one embodiment, the hook material of urine bag 1 attachment device 3 comprises a low profile material obtained from Aplix, Inc. of Charlotte, N.C., and the hook friendly material of attachment device 3 (such as material 19 on inner side 11 of bag 1) is a #90, white loop, nylon tricot fabric obtained from the Oumiet Corporation of Nashville, Tenn.

In an alternate embodiment, sleeve 5 is "loop friendly", e.g., comprises, is coated with, bonded to, laminated to, or otherwise attached to, a hook fabric. Bag 1, which has loop material, is directly attached to sleeve 5 without using piece 7 to firmly hold bag 1 in place while causing it to conform to the shape of the wearer's leg.

To permit bag 1 to remain so conformed to the user's leg, even when filled, outer side 13 of bag 1 comprises pre-formed flexible tray 15 that is so formed prior to being sealed to the polyolefin, poly vinyl chloride, or polyethylene sheet that comprises inner side 11. This arrangement permits bag 1 to expand when filled in a single direction only, away from the leg, without forcing the edges of bag 1 to lift away from the leg (thereby preventing the discomfort and embarrassment normally associated with the inflation of many urine bags). In addition, tray 15 is self-supporting. Tray 15 includes pleats 17, which tend to fold and unfold with the emptying and filling of bag 1, much like an accordion expands and contracts. To maintain as low a profile as possible for the bag, formed side 13 is molded to incorporate pleats that would open only as and when bag 1 is filled.

Tray 15 is made of polyolefin, poly vinyl chloride or polyethylene. Any material suitable for constructing a self-supportive tray that expands to a preformed dimension can be used, however. Because of the design approach taken, bag 1 can be made of a light-gauge material, and its overall size is reduced since no provision need be made for the attachment of straps. These factors permit a less expensive bag, which in turn permits the bag to be fully disposable on a daily basis. Daily replacement is not only more convenient for users, who often wash and reuse conventional bags for many days in a row, but helps prevent infections that can result from such reuse.

Urine flows into bag 1 through flutter valve 31 until bag 1 is full. Any suitable flutter or ribbon valve can be used for valve 31. For example, in one embodiment valve insert 33 uses a flutter valve such as described in U.S. Pat. No. 4,828,554, which is hereby incorporated by reference in its entirety.

Bag 1 is emptied at non-drip outlet 40 through non-drip quick connect fittings/valves 53 and 55, which comprises two connector pieces that are respectively attached to outlet 40 and tube 56, and mate to create a flow-through connection. Any non-drip quick connect fitting or other connection suitable for connecting medical conduits can be used, however. To facilitate the use of bag 1 with pump 51 (or without), outlet fitting/valve 53 and pump inlet fitting/valve 55 include non-drip quick connect fittings, such as one disclosed in U.S. Pat. No. 4,436,125, which is hereby incorporated by reference in its entirety. Where suitable, other connection points may exist where such fittings are used. While being filled, while full, and while being emptied, bag 1 conforms to the user's leg.

Pump 51 uses battery 93 but becomes operational only after it is removed from magnetic mount 87 and only while separate switch 89 is activated. Such a dual-switch safety switch design is disclosed in U.S. Pat. No. 4,402,138, which is hereby incorporated by reference in its entirety.

Outlet 40 of bag 1 is connected via tubing to inlet 55 of pump 51, and pump outlet 57 is connected by tubing to flexibly-shaped-but-rigid wand 81, which holds its shape upon bendable reconfiguration. Wand 81 has check valve 91 at its end which prevents the flow of urine unless actively under positive pressure from pump 51. This feature prevents urine from dripping from wand 81 after pump 51 is turned off.

In one embodiment, a 2 PSI spring on a fitting/check valve 53 at the outlet 57 side of pump 51 keeps pressure exerted on bag 1 from forcing urine through pump 51 and out the end of wand 91 when pump 51 is off.

Referring to FIGS. 1 and 1*a*, to prevent sticking between the inner walls of inner side 11 and outer side 13 of bag 1 when emptied, and to prevent such sticking from negatively affecting flutter valve 31, several features have been added. First, outlet end 30 of flutter valve 31 has a shroud, e.g., it is enclosed within rectangular casing 37, both of which form plastic valve insert 33 used at bag's 1 inlet 35. By shrouding flutter valve 31 with rectangular casing 37, no pressure may be exerted against its sides by the sides of bag 1. Thus, after catheter outlet tube 21 is fit onto inlet end 32 of flutter valve 31, urine freely flows through flutter valve 31 and into the space inside of bag 1 defined by casing 37. Second, casing 37 accordingly further allows an amount of urine to flow into bag 1 that is sufficient in weight to help counteract the surface tension and sticking that might exist between bag sides 11 and 13, especially when the urine dries.

In one embodiment, bag 1 is partially assembled by the user, who before use, inserts valve insert 33, which is pre-coated with a suitable adhesive, into an inlet 35 of tray 15. One half of non-drip quick connect fitting/valve 53 is also inserted by the user into outlet 40. Suitable adhesives include any substance capable of being safely used to attach the above-mentioned component parts by an end-user.

Referring again to FIG. 1, another feature that prevents sticking between sides 11 and 13 is sheet 41. By inserting thin sheet of reticulated foam 41 between the inner 11 and outer 13 sides of bag 1, the two flat, wet internal surfaces of sides 11 and 13 are prevented from coming in contact with one another. Foam sheet 41 is made from polyurethane or polyester. Casing 37 and sheet 41 additionally provide the following: when bag 1 is being used as part of the larger apparatus described herein, pump 51, described below, is not able to fully empty bag 1 of air, thereby assisting in keeping reusable (emptied) bag 1 readily available for refilling, without risk of messy and potentially dangerous catheter back flow or stoppage.

Protective cloth flap 71 sewn onto fabric sleeve 5 at seam 72, operatively covers bag 1 according to directions arrows X to help prevent any inadvertent damage to the bag during use (e.g., helps reduce the potential risk of accidental punctures). Hook material 77 sewn onto the underside of flap 71 attaches to sleeve 5 to securely fit protective flap 71 over bag 1.

Flap 71 further contains wireless, battery powered pressure sensor 73, which is used to signal a user that the bag is full and in need of being emptied. Sensor 73, which is sewn into the inside of flap 71, operates in conjunction with electronic transponder 75, which indicates that bag 1 is full. This feature may be of particular benefit to those who are seriously disabled and unable to make such a determination via their own senses.

It is understood that bag 1 is suitable for use with any bodily fluid and waste in addition to, or in lieu of, urine.

Referring to FIGS. 1*a*, 1*b*, and 1*c*, in an alternate embodiment unitary preformed tray 19 (seen in FIG. 1*c*), which has predefined seams 101, is attached to inner side 11 to form a urine bag. Unlike accordion-like tray 15, tray 19 collapses onto itself in a less regular fashion when emptied. Tray 19 is made of plastic that has been molded to create relatively reinforced seams 101. One way to make such a tray is by blow molding plastic into a mold that leaves room for the formation of edges that are substantially thicker than the five tray walls. In an alternate embodiment, living hinges are used as the seams of tray 19 or as the accordion edges 17 of tray 15. Any materials and designs suitable for constructing a self-supportive tray that expands to a preformed dimension can be used, however.

At inlet 117 tray 19 includes inner plastic sheath 107, which receives and adheres to rectangular valve insert 33 (seen in FIG. 1a). Thus, circular sheath 107 at inlet 117 operatively connects casing 37 of rectangular valve insert 33 to inlet 117, inside of tray 19.

In an alternate embodiment shown in FIGS. 1b and 1c, valve 31 is enclosed within concentric circular casing 47, which is formed as part of plastic valve insert 43 used as inlet 45. Before use, valve insert 43 is inserted by the user into sheath 107 at tray inlet 117, and one half of circular outlet quick connect fitting/valve 53 is inserted by the user into sheath 105 of outlet 115. Thus, inner plastic sheath 107 receives and adheres to circular valve insert 43, and circular sheath 107 operatively connects casing 47 of circular valve insert 43 to inlet 117, inside of tray 19. Tray 19 also includes inner plastic sheath 105 at outlet 115, which receives and adheres to a portion of a non-drip quick connect fitting, such as fitting/valve 53 shown in FIG. 1. It is important to note that trays 15, 19, and other trays suitable for use in other embodiments of this invention can be adapted for use with either valve insert 33, 43, or any other valve insert suitable for receiving a flow of liquid into the urine bags contemplated by this invention.

Figure 2:
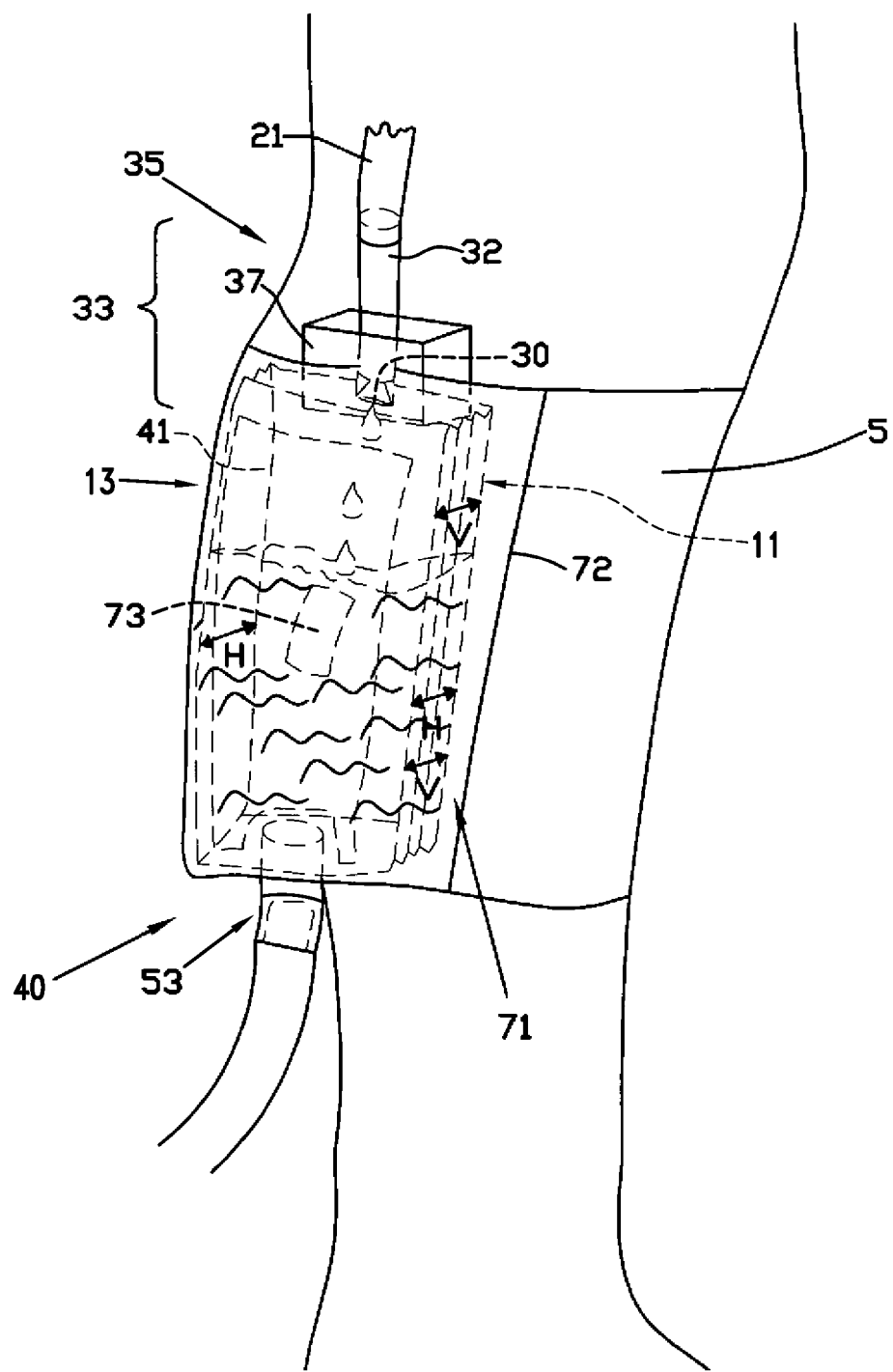
FIG. 2 is a perspective view of the attachment device for a urine receptacle and the urine receptacle of FIG. 1, as attached to a wearer and half-full of urine.

Referring to FIG. 2, once bag 1 is attached and substantially filled, the distance between inner 11 and outer 13 sides does not substantially vary, either along a vertical or horizontal distance, as shown by respective distance arrows V and H. Hence, inner 11 and outer 13 sides remain substantially parallel as bag 1 is empty, is being filled, and is full. Moreover, bag 1 is self supporting so that its shape is not dependant upon an enclosing pouch or other receptacle. This provides accessibility for ease of use and replacement, and enhanced comfort.

Figure 3:
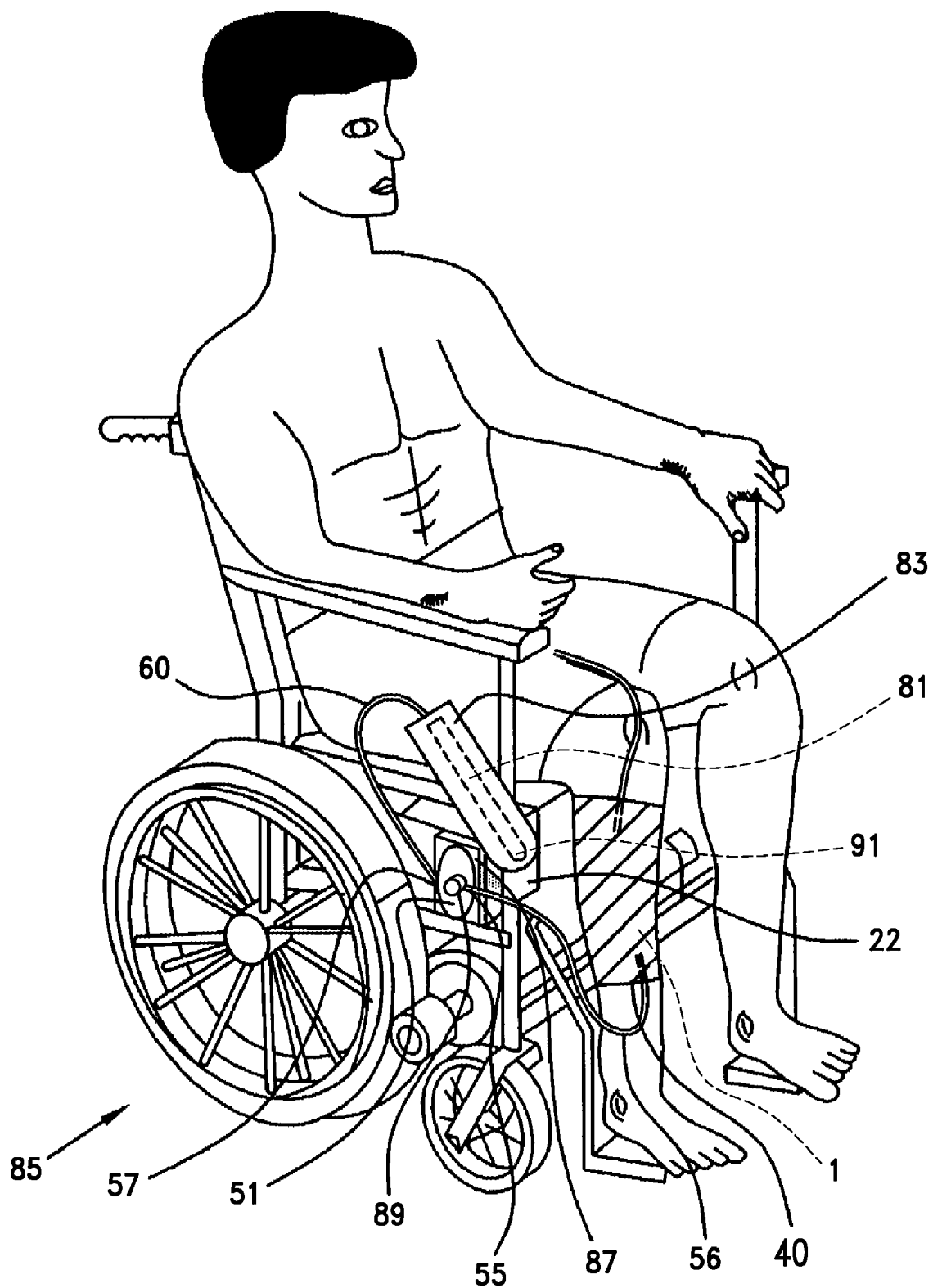
FIG. 3 is a perspective view of the attachment device, the urine receptacle, and the apparatus for disposing urine of FIG. 1, as worn and used in conjunction with a wheel chair, according to the present invention.

Referring to FIG. 3, in one embodiment, which assists those in wheel chairs who are unable to empty conventional bags easily, the system includes pump 51, which is powered by either chair battery 22 or a separate rechargeable battery pack. Outlet 40 of bag 1 is connected via tubing 56 to inlet valve 55 of pump 51, and pump outlet 57 is connected by tubing 60 to wand 81, which is removably stowed in sheath 83 on wheel chair 85.

The user will be able to free wand 81 from its stowed position, direct the projected flow of urine into a urinal or toilet, and activate pump 51 to empty bag 1. This feature will allow a wheel chair-bound user to empty bag 1 without assistance in any restroom into which chair 85 may venture. Access to a handicapped stall, for example, would not be required. The ability to empty bag 1 when full is of critical health importance, and use of pump 51 ensures that the user will be able to do so as and when necessary and without requiring the assistance of another person.

As discussed above, pump 51 becomes operational only after it is removed from magnetic mount 87 and only while separate switch 89 is activated. Any switch controlled by a position sensor that is sufficient to prevent activation when the wand is in the stowed position if switch 89 is inadvertently activated, however, is suitable as well.

Figure 4:
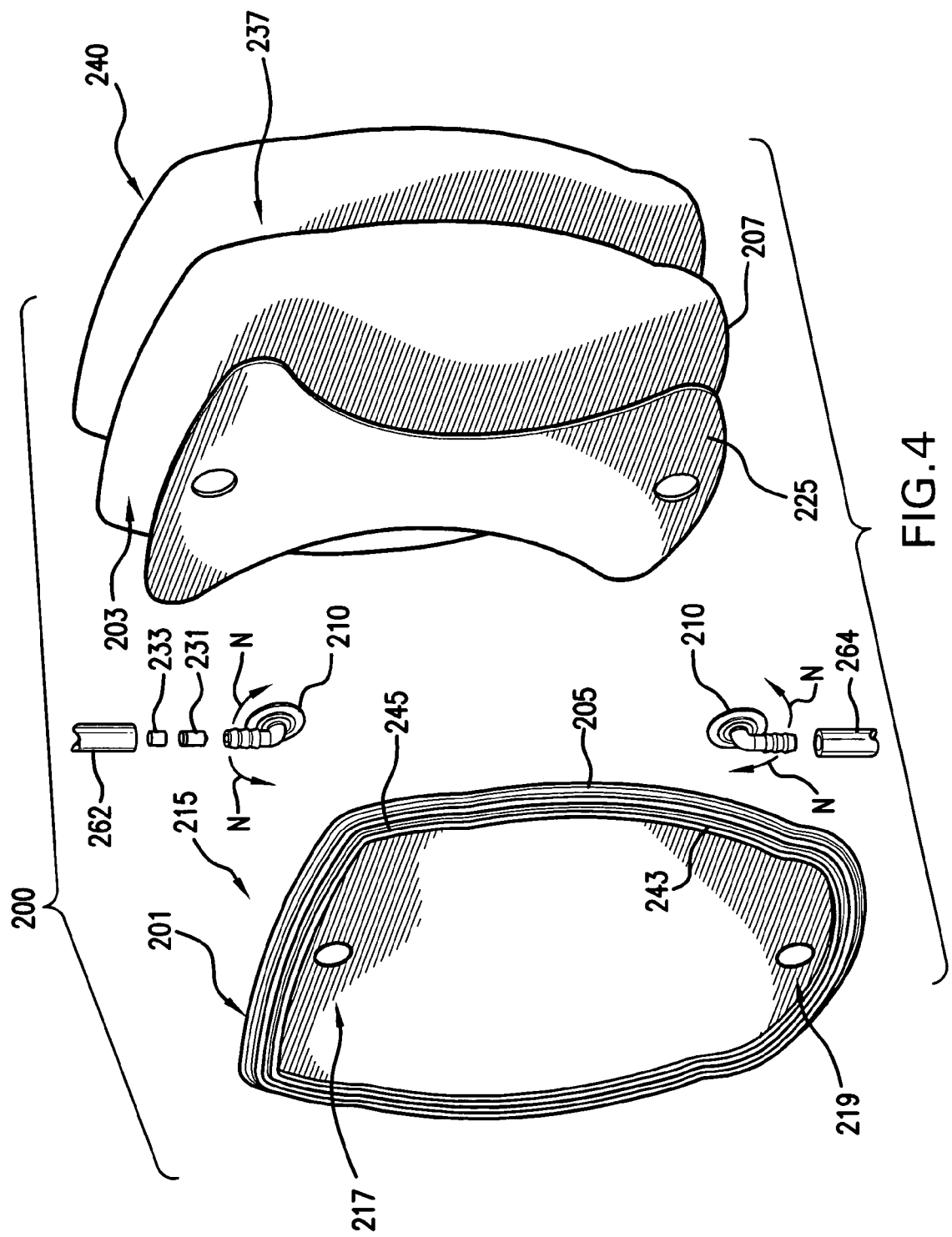
FIG. 4 is a perspective assembly view of a urine receptacle, which includes swiveling inlet and swiveling outlet nozzle assemblies, a one-way inlet valve and filter, end portions of inlet and outlet tubes, and an attachment backing, according to the present invention.

Referring to FIG. 4, in one embodiment urine bag 200 includes upper shell 201 and lower shell 203, which are attached at their respective external edges 205 and 207. Sandwiched between shells 201 and 203 are inlet and outlet nozzle assemblies 210, which are fed through respective upper inlet opening 217 and lower outlet opening 219 on upper shell 201 and attached to inside surface 215 of upper shell 201. Also sandwiched between upper 201 and lower 203 shells is foam liner 225, which prevents upper and lower shells from sticking to one another when bag 200 is emptied. Foam liner 225 has a hourglass shape, which uses less material than a liner that rests between the entire width of upper 201 and lower 203 shells, but it nevertheless protects the direct pathway between inlet opening 217 and outlet opening 219.

Attached to back side 237 of lower shell 203 is hook friendly, cloth backing 240, which in one embodiment is adhesively bonded to lower shell 203 and attached on its opposing side to mating hook material worn on the user's leg.

As described in detail below, nozzle assemblies 210 provide swivel action in accordance with direction arrows N to point approximately along the longitudinal direction of respective inlet 262 and outlet 264 tubes.

Figure 5:
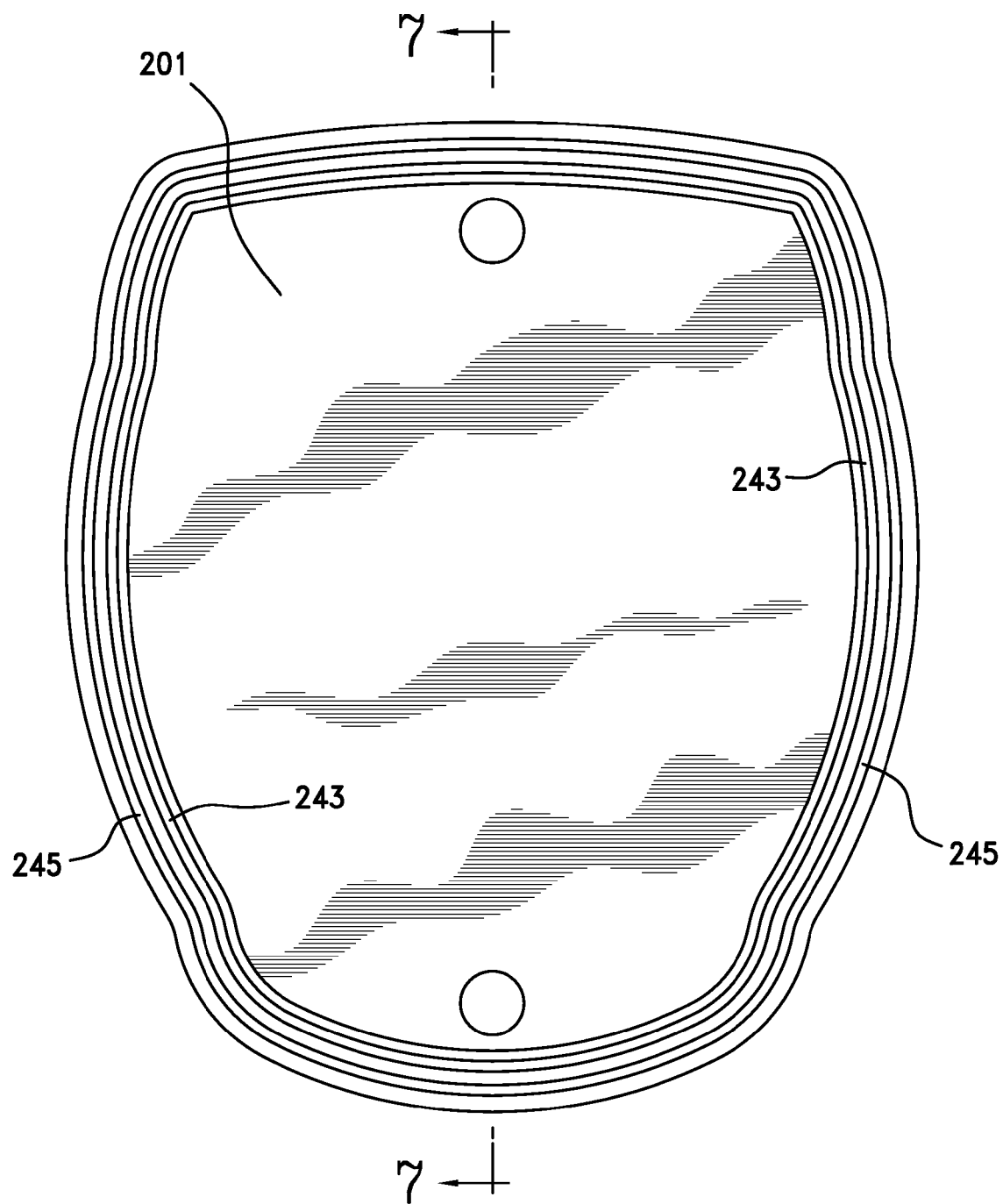
FIG. 5 is a front plan view of the outer shell of the urine receptacle of FIG. 4.

Referring to FIG. 5, upper shell 201 comprises concentric rings 243 and 245. Shell 201, including rings 243 and 245, is formed from plastic such as polyolefin, polyvinyl chloride, or polyethylene. Other suitable materials include, but are not limited to, other plastics. Other suitable construction designs also include any plastics that can be formed into a living hinge. Any flexible, fluid-containing material suitable for expanding and contracting to receive and be emptied of urine, however, can be used.

Figure 6:
FIG. 6 is a side plan view of the outer shell of FIG. 5.

Referring to FIG. 6, as seen along its exterior side 241, upper shell 201 is collapsible and expandable to hold a volume of urine, in accordance with the separation of collapsing and expanding concentric rings 243 and 245.

Figures 7, 8:
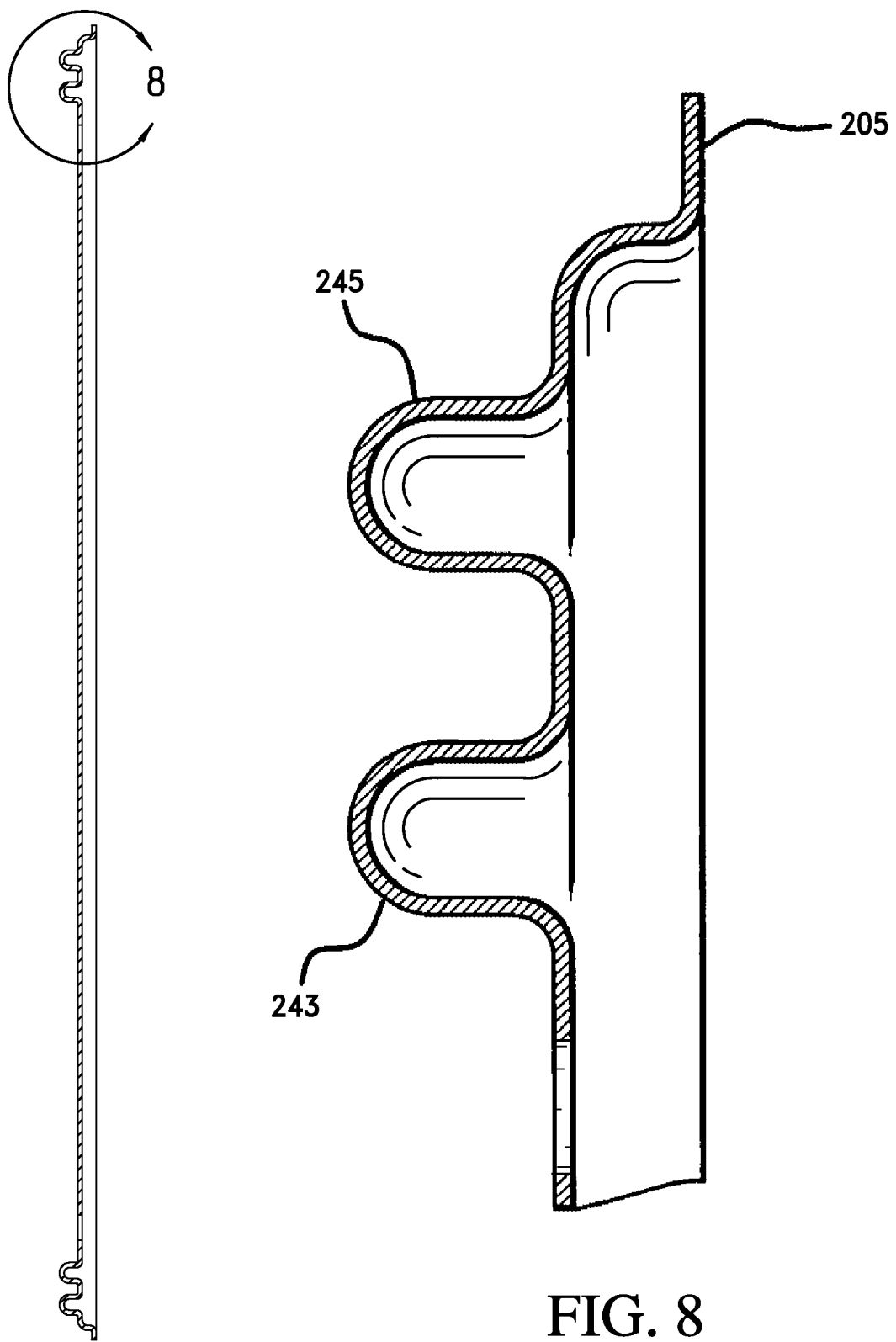
FIG. 7 is a cross-sectional plan view of the outer shell of FIG. 5, along the line 7-7.
FIG. 8 is a close-up partial plan view of the outer shell of FIG. 7 encircled by line 8.

Referring to FIG. 7, as seen along bisecting line 7-7 of FIG. 5, concentric rings 243 and 245 comprise separate ridges formed in the material of shell 201.

Referring to FIG. 8, these ridges are formed by either thermoforming, vacuum forming, or a combination of the two processes.

Referring to FIG. 9, inlet nozzle assembly 210 enhances liquid flow by aligning the axis of nozzle fitting 255 with the direction of flow toward, and away from, the urine bag. Inlet nozzle assembly 210 includes elbow nozzle fitting 255, gasket ring 253, and nozzle attachment ring 251, which is secured to inside surface 215 of upper shell 201 (as shown in FIG. 4). Elbow nozzle fitting 255 swivels about attachment ring 251 as the position of the inlet tube changes. Thus, the swivel action of assembly 210 provides a continuous and adjustable alignment of the longitudinal axis of fitting 255 with the longitudinal axis of the urine inlet tube. This swivel-action thereby enhances the ease of flow of urine from the direction of a catheter insertion or attachment point to the bag by preventing kinks in the tubing, or other fluid pathways, that occur because of inlet-to-tubing misalignment.

Used as an outlet, nozzle assembly 210 likewise enhances flow by swiveling fitting 255 about attachment ring 251 and towards the outlet tube. This movement better aligns fitting's 255 longitudinal axis with the longitudinal axis of an outlet tube, and in fact provides a continuous and adjustable alignment. Although fitting 255 provides all of these benefits, any fitting, mechanism, or device that provides adjustable, continual, or continuous alignment can be used.

Elbow inlet fitting 255 also encases one-way cartridge check valve 231, and thereby shrouds, and prevents impingement upon, valve 231. In one embodiment, check valve 231 is a Model 110 valve manufactured by Smart Products, Inc. of Morgan Hill, Calif.

Inside of fitting 255 is cylindrical fiber or foam filter 233, which reduces particulates that may interfere with valve closure within the system, and one-way cartridge valve 231. In one embodiment, filter 233 is a fiber filter cartridge.

Referring to FIG. 10, in one embodiment semicircular valve 300 is used. Valve 300 tapers at its outlet end 302, somewhat like a traditional flutter valve. Unlike a traditional flutter valve, however, valve's 300 outlet end 302 is formed into semicircle end portion 304 on one side. On the other side, flap 306 rests, collapsed within semicircle end portion 304.

Referring to FIG. 11, when semicircular valve 300 is inflated by fluid flow, it expands to a diameter equal to the diameter of the semicircle. As fluid flows into outlet end 302, flap 306 moves in accordance with direction arrows Q to form a circular passage through which the liquids flow.

Referring to FIGS. 10 and 12, when inflated, semicircular valve 300 thus has an outside diameter T, which closely approximates the inside diameter E of fitting 255. Thus, when semicircular valve 300 is placed within a shroud such as cylindrical fitting 255, its internal diameter S is slightly smaller than internal diameter E of fitting 255. As a result, the volume of liquid that can flow without restriction through form fitting semicircular valve 300 is far greater than the volume that can flow through a traditional flutter valve placed within the same shroud, e.g., fitting 255. In applications where flow rates are critical and where shroud size is limited, semicircular valve 300 offers superior benefits when compared to traditional valves.

Semicircular valve 300 is made from latex that is dip molded using an asymmetrically tapering cylindrical mandrel. Other embodiments include valves having a living hinge. Any combination of material and valve shape suitable for conforming, or nearly conforming, to the internal dimensions of a shroud, or that is of unitary, monolithic, or multiple piece construction, can be used, however.

A second aspect of the present invention is directed to an apparatus for automated disposal of human waste fluid such as urine, which comprises the various elements as substantially described above.

For example, one embodiment is directed to an apparatus for automatic disposal of human waste fluid that operatively uses a urine receptacle that conforms to the wearer's body and does not lift apart from the wearer as it is filled.

While it is apparent that the illustrative embodiments of the invention disclosed herein fulfill the objectives of the present invention, it is appreciated that numerous modifications and other embodiments may be devised by those skilled in the art. Additionally, feature(s) and/or element(s) from any embodiment may be used singly or in combination with other embodiment(s). Therefore, it will be understood that the appended claims are intended to cover all such modifications and embodiments that would come within the spirit and scope of the present invention.

I claim:

1. A urine receptacle, comprising:
    a first side that operatively conforms to a wearer's body;
    a collapsible second side that expands as the receptacle is filled; and
    at least one protrusion or depression, that flexes to allow the receptacle to expand;
    wherein the receptacle is self-supporting and, once the receptacle is attached and substantially filled, the distance between the first side and the second side does not substantially vary along a horizontal length that runs from the at least one protrusion or depression at a first edge of the receptacle to the at least one protrusion or depression at a diametrically opposing second edge of the receptacle, and the distance between the first side and the second side does not substantially vary along a vertical length that runs from the at least one protrusion or depression at a third edge of the receptacle to the at least one protrusion or depression at a diametrically opposing fourth edge of the receptacle.

2. The urine receptacle of claim 1 wherein the first side and the second side remain substantially parallel as the receptacle is empty, is being filled, and is full.

3. The urine receptacle of claim 1 wherein the second side comprises a pre-formed tray.

4. The urine receptacle of claim 3 wherein the tray has concentric ridges.

5. The urine receptacle of claim 4 wherein the first side has a perimeter that is operatively attached to a sleeve, which is configured to be on a wearer's leg, by hook and loop fasteners.

6. The urine receptacle of claim 5 wherein the second side and the sleeve comprise hook compatible surfaces that are mated by a piece having double-sided hook material.

7. The urine receptacle of claim 1 wherein the receptacle has a spacer that keeps the first and second sides from adhering to each other.

8. The urine receptacle of claim 1 wherein the receptacle has an inlet valve encased by a shroud that prevents interference with the valve.

9. The urine receptacle of claim 1 wherein the receptacle is reusable and is operatively connected to a device for automatically disposing urine.

10. The urine receptacle of claim 9 wherein the receptacle is operatively connected to the device by at least one non-drip fitting.

11. The urine receptacle of claim 9 wherein the receptacle has an outlet that is operatively connected to a pump that works to empty the receptacle.

12. The urine receptacle of claim 11 wherein the pump has a safety switch and is mounted onto a wheelchair.

13. The urine receptacle of claim 9 wherein the receptacle is operatively connected to a waste-directing wand.

14. An apparatus for automatic waste disposal, comprising:
    a receptacle having a first side that operatively conforms to a wearer;
    a collapsible second side that expands as the receptacle is filled; and
    at least one protrusion or depression, that is generally perpendicular with respect to the first or second side and flexes to allow the receptacle to expand;
    wherein the receptacle is self-supporting and, once the receptacle is substantially filled, the distance between the first side and the second side does not substantially vary along a horizontal length that runs from the at least one protrusion or depression at a first edge of the receptacle to the at least one protrusion or depression at a diametrically opposing second edge of the receptacle, and the distance between the first side and the second side does not substantially vary along a vertical length that runs from the at least one protrusion or depression at a third edge of the receptacle to the at least one protrusion or depression at a diametrically opposing fourth edge of the receptacle.

15. The apparatus of claim 14 wherein the first side and the second side remain substantially parallel as the receptacle is empty, is being filled, and is full.

16. The apparatus of claim 14 wherein the second side comprises a pre-formed tray.

17. The apparatus of claim 16 wherein the tray comprises a polyolefin, polyester, or polyvinylchloride film.

18. The apparatus of claim 14 wherein the first side has a perimeter that is operatively attached to a sleeve, which is configured to be on a wearer's leg, by hook and loop fasteners.

19. The apparatus of claim 18 wherein the second side and the sleeve comprise hook compatible surfaces that are mated by a piece having double-sided hook material.

20. The apparatus of claim 14 wherein the receptacle has a spacer that keeps the first and second sides from adhering to each other.

21. The apparatus of claim 14 wherein the receptacle has a one-way inlet valve encased by a shroud fitment to which an inlet tube or catheter is attached.

22. The apparatus of claim 14 wherein the receptacle is reusable and is operatively connected to a device for automatically disposing urine.

23. The apparatus of claim 22 wherein the receptacle is operatively connected to the device by at least one non-drip fitting.

24. The apparatus of claim 22 wherein the receptacle has an outlet that is operatively connected to a pump that works to empty the receptacle.

25. The apparatus of claim 24 wherein the pump has a safety switch and is mounted onto a wheelchair.

26. The apparatus of claim 22 wherein the receptacle is operatively connected to a waste-directing wand.

27. A urine receptacle, comprising:
a first side that operatively conforms to a wearer;
a collapsible second side that expands as the receptacle is filled; and
at least one generally circumferential protrusion or generally circumferential depression, that is generally perpendicular with respect to the first or second side and flexes to allow the receptacle to expand;
wherein the receptacle is self-supporting and the second side comprises a pre-formed, expandable tray; and once the receptacle is substantially filled, the distance between the first side and the second side does not substantially vary along a horizontal length that runs from the at least one generally circumferential protrusion or generally circumferential depression at a first edge of the receptacle to the at least one generally circumferential protrusion or generally circumferential depression at a diametrically opposing second edge of the receptacle, and the distance between the first side and the second side does not substantially vary along a vertical length that runs from the at least one generally circumferential protrusion or generally circumferential depression at a third edge of the receptacle to the at least one generally circumferential protrusion or generally circumferential depression at a diametrically opposing fourth edge of the receptacle.

28. The urine receptacle of claim 27 wherein the first side does not expand.

29. The urine receptacle of claim 27 wherein the pre-formed tray contracts as the receptacle is emptied of liquid.

30. The urine receptacle of claim 27 further comprising an inlet fitting that is configured to align a receptacle inlet with a catheter attachment or insertion point.

31. The urine receptacle of claim 30 wherein the fitting is an elbow fitting that swivels to allow alignment of the inlet with the catheter attachment or insertion point.

32. A urine receptacle, comprising:
a receptacle that conforms to a user's body, and comprises;
a side member that expands as the receptacle is filled; and
at least one generally circumferential protrusion or at least one generally circumferential depression, that is generally perpendicular with respect to the side member that expands and that flexes to allow the receptacle to expand;
wherein the receptacle is self-supporting, and the expanding side comprises a pre-formed, expandable tray; and once the receptacle is substantially filled, the distance between the first side and the second side does not substantially vary along a horizontal length that runs from the at least one generally circumferential protrusion or the at least one generally circumferential depression at a first edge of the receptacle to the at least one generally circumferential protrusion or the at least one generally circumferential depression at a diametrically opposing second edge of the receptacle, and the distance between the first side and the second side does not substantially vary along a vertical length that runs from the at least one generally circumferential protrusion or the at least one generally circumferential depression at a third edge of the receptacle to the at least one generally circumferential protrusion or the at least one generally circumferential depression at a diametrically opposing fourth edge of the receptacle.

33. The urine receptacle of claim 32 wherein the pre-formed expandable tray has at least two concentric ridges comprising the at least one generally circumferential protrusion and/or the at least one generally circumferential depression.

34. The urine receptacle of claim 32 wherein the at least one generally circumferential protrusion or the at least one generally circumferential depression comprises an inner concentric and entirely circumferential protrusion or an inner concentric and entirely circumferential depression, and wherein the horizontal and vertical lengths are both co-planar with a generally flat portion of the side member that moves as the side member expands, said generally flat portion directly connecting opposing portions of the inner concentric and entirely circumferential protrusion or the inner concentric and entirely circumferential depression.

* * * * *